(12) United States Patent
Marine et al.

(10) Patent No.: US 11,529,094 B2
(45) Date of Patent: Dec. 20, 2022

(54) SYSTEM, METHOD, AND APPARATUS FOR TEMPERATURE ASYMMETRY MEASUREMENT OF BODY PARTS

(71) Applicant: UAB Diabetis, Vilnius (LT)

(72) Inventors: Gintare Marine, Vilnius (LT); Urte Steikuniene, Vilnius (LT); Jonas Guzaitis, Kaunas (LT); Rytis Zajanckauskas, Vilnius (LT)

(73) Assignee: Diabetis, Vilnius (LT)

( * ) Notice: Subject to any disclaimer, the term of this patent is extended or adjusted under 35 U.S.C. 154(b) by 0 days.

(21) Appl. No.: 17/374,282

(22) Filed: Jul. 13, 2021

(65) Prior Publication Data

US 2021/0338148 A1 Nov. 4, 2021

Related U.S. Application Data

(63) Continuation-in-part of application No. 17/155,647, filed on Jan. 22, 2021, which is a continuation-in-part (Continued)

(51) Int. Cl.
*A61B 5/00* (2006.01)
*A61B 5/01* (2006.01)

(52) U.S. Cl.
CPC .......... *A61B 5/4528* (2013.01); *A61B 5/0077* (2013.01); *A61B 5/015* (2013.01)

(58) Field of Classification Search
CPC ..... A61B 5/4528; A61B 5/0077; A61B 5/015; A61B 5/0035
See application file for complete search history.

(56) References Cited

U.S. PATENT DOCUMENTS

| 7,924,312 B2 | 4/2011 | Packard |
| 2006/0062448 A1* | 3/2006 | Hirsch .................. G06V 40/11 382/154 |

(Continued)

FOREIGN PATENT DOCUMENTS

WO 2015143218 A1 9/2015

OTHER PUBLICATIONS

"Thermal and Visual Imaging and Accelerometry Development to Assist with Arthritis Diagnosis" by H.U. Nwaizu. Sheffield Hallam University. Apr. 6, 2019 (Year: 2019).*

(Continued)

*Primary Examiner* — Jason M Ip

(57) ABSTRACT

System, apparatus, and method for automatic detection of arthritis according to temperature asymmetry estimation in contralateral joints is presented. Simultaneously recorded thermogram and the optical image of an inspected joint and its contralateral joint are sent to the processing unit, where they are stored, processed, and analyzed. The system, apparatus, and method automatically detects outlines of joints in thermograms and optical images. Grid of points of interest is distributed inside the inspected and the contralateral joint's outline. Temperature maps are calculated according to both grids points and the temperature disparity map is estimated. The set of inflammation regions is obtained by analyzing the temperature disparity map and collecting adjacent points containing temperature differences surpassing the threshold. The system, apparatus, and method are non-invasive and non-contact, and suitable for real world environments with natural home or health care institutions background.

18 Claims, 8 Drawing Sheets

Related U.S. Application Data of application No. 16/646,103, filed as application No. PCT/IB2020/051950 on Mar. 6, 2020.

(56) References Cited

U.S. PATENT DOCUMENTS

| | | |
|---|---|---|
| 2013/0261494 A1 | 10/2013 | Bloom et al. |
| 2013/0261495 A1 | 10/2013 | Linders et al. |
| 2013/0261496 A1 | 10/2013 | Engler et al. |
| 2015/0057562 A1 | 2/2015 | Linders et al. |
| 2015/0190059 A1 | 7/2015 | Petersen et al. |
| 2016/0100790 A1 | 4/2016 | Cantu et al. |
| 2016/0150976 A1 | 6/2016 | Fang et al. |
| 2016/0183879 A1 | 6/2016 | Goldish et al. |
| 2016/0192844 A1 | 7/2016 | Linders et al. |
| 2016/0256056 A1 | 9/2016 | Petersen et al. |
| 2017/0127999 A1 | 5/2017 | Linders et al. |
| 2017/0150888 A1* | 6/2017 | Millikan ............... G01J 3/0208 |
| 2018/0107798 A1* | 4/2018 | Hu .......................... G16H 10/20 |
| 2018/0132726 A1 | 5/2018 | Dickie et al. |
| 2020/0113510 A1 | 4/2020 | Linders et al. |
| 2020/0121245 A1 | 4/2020 | Barclay et al. |

OTHER PUBLICATIONS

"Mutual information based detection of thermal profile in hand joints of rheumatoid arthritis patients using Non-parametric windows" by A. Nouri et al. 2001 IEEE Canadian Conference on Electrical and Computer Engineering. May 2016 (Year: 2016).*

International Search Report and Written Opinion dated Nov. 3, 2020 in International Application PCT/IB2020/051950.

Chanjuan Liu et al., "Automatic detection of diabetic foot complications with infrared thermography by asymmetric analysis," Journal of Biomedical Optics, SPIE, vol. 20, No. 2, Feb. 1, 2015, p. 26003.

* cited by examiner

SYSTEM, METHOD, AND APPARATUS FOR TEMPERATURE ASYMMETRY MEASUREMENT OF BODY PARTS

CROSS REFERENCE TO RELATED APPLICATIONS

This application is a continuation-in-part of U.S. patent application Ser. No. 17/155,647, titled System, Method, And Apparatus For Temperature Asymmetry Measurement Of Body Parts and filed on Jan. 22, 2021, which is a continuation-in-part of U.S. application Ser. No. 16/646,103, titled System, Method, And Apparatus For Temperature Asymmetry Measurement Of Body Parts and filed on Mar. 10, 2020, which is a National Stage Entry of PCT/IB2020/051950, titled System, Method, And Apparatus For Temperature Asymmetry Measurement Of Body Parts and filed on Mar. 6, 2020. The entire contents of all referenced applications are hereby incorporated by reference in their entirety.

BACKGROUND

1. Field

The present disclosure relates to systems, methods, and apparatus for thermal imaging in medical applications and, more particularly, to temperature asymmetry estimation of body parts.

2. Description of the Related Art

Generally, one's body temperature is greater than the ambient temperature. Certain techniques, such as infrared thermal imaging, enable temperature maps of human body or other animal body parts to be produced. When a person experiences a disease or a functional change affecting a body part, temperature of the affected body part may be significantly different compared to that of normal tissue. Inflammation, pre-cancerous tissue formation, tumor growths, and other factors may increase affected body part temperature, while diseases such as vasculitis or artery sclerosis may decrease affected body part temperature.

For example, Rheumatoid Arthritis (RA) can be diagnosed by detecting an elevated dermal temperature over an inflamed joint of a patient. RA is an autoimmune systemic connective tissue disease, the cause of which has not yet been fully explained. Factors such as genetics, the environment, and infectious and autoimmune disorders play an important role in the etiopathogenesis of RA. Many types of immune cells and their cytokines, proteinases, and growth factors mediate inflammation, joint destruction, and systemic complications that lead to disability and premature death. The heterogeneous character of the disease renders it impossible to predict its progress. RA has a chronic course with periods of exacerbation and remission. RA is characterized by nonspecific inflammation of the symmetrical joints and the occurrence of joint swelling, joint tenderness, and destruction of the synovial joint.

Medical thermal imaging provides information on the functioning of the superficial dermal microcirculation that is affected by local inflammatory processes. The pathological changes can be manifested by the heat radiation of tissues and organs, which transpose to the surface regions. These subtle temperature changes may be recorded by infrared thermography and then be objectively evaluated after pharmacological, physical, or surgical treatment.

Many sources have reported that the use of thermovision techniques (i.e., to measure or detect temperature information corresponding to a body) is a very useful tool in the examination of patients. In rheumatology, infrared imaging is used to detect the increased temperature associated with inflammation or decreased temperature caused by nociceptive afferentation or obstruction of vessels. This method may also be used to monitor temperature changes after pharmacotherapy and other therapeutic methods of treatment and to observe microcirculation.

However, the temperature differences for RA regions are small, challenging to monitor, and difficult to determine using analog means, and are not widely monitored in the current medical practice for RA monitoring.

The infrared thermal imaging is a preferable and useful way to record temperature maps because it is a non-invasive and non-contact technology that acquires thermal images based on the emitted heat (thermal energy) from the body. Thermal radiation includes electromagnetic waves from the Long Wavelength Infrared (LWIR) range 0.000314 inches to 0.000551 inches (8 micrometers ($\mu$m) to 14 $\mu$m). The infrared techniques allow rapid capturing of a relatively large quantity of pixels or picture elements. The individual pixels at the respective points denote the local temperature, and the collection of these pixels create an image illustrating the surface temperature distribution. Infrared thermal imaging has made it possible to measure or detect an increased temperature that occurs in some regions of the body. It was determined that a temperature increase within one joint, compared to the contralateral joint's mean temperature, requires an accurate assessment in order to decide whether it is an occurrence of RA inflammation. Monitoring such differences through thermal images captured with the use of infrared thermography devices may prove to be an efficient way of detecting and monitoring RA inflammation.

Patent document US20100191124A1 (application filing date of 2008-04-15) provides a system and a method for using three-dimensional infrared imaging to provide psychological maps of individuals. Calibrated infrared and range imaging sensors are used to produce a true-metric three-dimensional (3D) surface model of any region of the body within the fields of view of both sensors. Curvilinear surface features in both modalities are caused by internal and external anatomical elements. Features are classified by origin, location, and characteristics to produce annotations that are recorded with the images and feature maps in reference image libraries. However, the method is not sensitive enough to detect minor changes in person's body temperature, such as inflammation caused by arthritis. Also, the method does not use both left and right leg joints or other body parts' temperature data values for comparing the temperature differences. Therefore, it is not suitable for detecting inflammation, diseases, or functional disorders.

Current technologies, which use non-contact thermal imaging of the person's body parts for detection of inflammation, do not have an automatic way of distinguishing a body part outline from a surrounding background. They use such solutions as covering body parts of a non-monitored person with a damp cold towel, placing the person in a large box, etc. Existing methods fail to allow for monitoring and detecting of inflammation, diseases, or functional disorders which have slightly increased local temperature maps.

Thus, an advanced self-assessment tool to monitor contralateral joints of people to detect arthritis is needed.

SUMMARY

A system, method, apparatus, and use of the system, method, and apparatus are presented, which automatically detects regions of inflammation or functional disorder according to temperature asymmetry estimation in contralateral body parts. This is a non-invasive and non-contact body part inspection method. The method may be used to determine the inflammation or functional disorder regions between contralateral body parts or adjacent areas of a human or other animal. Simultaneously recorded thermogram and the optical image of the inspected and contralateral body parts are sent to the processing unit, where they are stored, processed and analyzed. The method automatically detects outlines of body parts in at least one thermogram and at least one optical image. Grid of points of interest are distributed inside the inspected outline of the body part, and the same grid with applied geometrical transformations is distributed inside the contralateral body part outline. Temperature maps are calculated according to both grids points and a temperature disparity map is estimated by subtracting the appropriate temperature values of inspected and contralateral temperature maps of the body parts. The set of inflammation regions is obtained by analyzing the temperature disparity map and collecting adjacent points containing temperature differences that surpass the threshold. The exact areas of inflammations are determined. Thus, the early onset of the disease or pre-disease state could be detected. The method could be used both at home and at healthcare institutions. There is no need to use any precautions (such as damp cold towel or screen) for background elimination. The method is capable of determining an outline of a body part in real world environments with natural home or health care institution backgrounds, which may include other objects that emit thermal radiation.

Disclosed herein is a method for detection of a health disorder based on temperature asymmetry estimation in contralateral or reference body parts. The method includes recording, using an optical camera and a thermal camera, an optical image and a thermogram corresponding to an inspected body part and a reference or contralateral body part; receiving, by a processing unit, the optical image and the thermogram; estimating, by the processing unit, a recorded image displacement based on the thermogram and the optical image; and determining, by the processing unit, that a functional disorder or inflammation of the inspected body part has occurred by comparing the thermogram corresponding to the inspected body part to the thermogram corresponding to the reference or contralateral body part based on the recorded image displacement.

In any of the foregoing embodiments, estimating the recorded image displacement includes localizing a template of the inspected body part by locating corresponding pairs of keypoints in the optical image and in the thermogram, and calculating a nonconformity error between the corresponding pairs of keypoints in the optical image and in the thermogram.

In any of the foregoing embodiments, estimating the recorded image displacement further includes fine tuning by fitting a shape of the inspected body part on the thermogram and the optical image.

In any of the foregoing embodiments, estimating the recorded image displacement further includes localizing a reference template of the reference or contralateral body part by locating corresponding pairs of reference keypoints in the optical image and in the thermogram, and calculating a nonconformity error between the corresponding pairs of reference keypoints in the optical image and in the thermogram.

In any of the foregoing embodiments, estimating the recorded image displacement further includes fine tuning by fitting a reference shape of the reference or contralateral body part on the thermogram and the optical image.

In any of the foregoing embodiments, the thermogram and the optical image are recorded simultaneously.

In any of the foregoing embodiments, determining that the functional disorder or inflammation of the inspected body part has occurred includes rejecting non-confident inflammation or functional disorder regions.

In any of the foregoing embodiments, determining that the functional disorder or inflammation of the inspected body part has occurred includes estimating temperature maps for the inspected body part and the reference or contralateral body part based on the thermogram of the inspected body part and based on the thermogram of the reference or contralateral body part.

In any of the foregoing embodiments, comparing the thermogram corresponding to the inspected body part to the thermogram corresponding to the reference or contralateral body part includes comparing the estimated temperature maps.

In any of the foregoing embodiments, the inspected body part is a joint/joints and the functional disorder or inflammation includes early detection of arthritis.

Also disclosed is a system for detection of a health disorder based on temperature asymmetry estimation in contralateral or reference body parts. The system may include a stand configured to rest on a surface and having a body part placement location configured to support or correctly place an inspected body part; an optical camera configured to detect image data corresponding to an inspected body part and a reference or contralateral body part, the optical camera further configured to be coupled to the stand; a thermal camera configured to detect a thermogram corresponding to the inspected body part and the reference or contralateral body part, the thermal camera further configured to be coupled to the stand; and a processor configured to receive the image data and the thermogram and to determine that a functional disorder or inflammation of the inspected body part has occurred by comparing the thermogram corresponding to the inspected body part to the thermogram corresponding to the reference or contralateral body part.

In any of the foregoing embodiments, the processor is further configured to estimate a recorded image displacement based on the thermogram and the optical image, and to determine that the functional disorder or inflammation has occurred based on the recorded image displacement.

In any of the foregoing embodiments, estimating the recorded image displacement includes localizing a template of the inspected body part by locating corresponding pairs of keypoints in the optical image and in the thermogram, and calculating a nonconformity error between the corresponding pairs of keypoints in the optical image and in the thermogram.

In any of the foregoing embodiments, the optical camera and the thermal camera are located on a mobile device, and the stand is configured to support the mobile device to direct the optical camera and the mobile camera towards the body part placement location.

In any of the foregoing embodiments, the mobile device further includes a network access device configured to transmit the thermogram and the optical image to the processor.

In any of the foregoing embodiments, the mobile device further includes a display configured to output data indicating that the functional disorder or inflammation of the inspected body part has occurred.

Any of the foregoing embodiments may further include a network access device configured to transmit data indicating that the functional disorder or inflammation of the inspected body part has occurred to a remote device associated with a healthcare worker.

Also disclosed is an apparatus for detection of a health disorder based on temperature asymmetry estimation in contralateral or reference body parts. The apparatus may include a base configured to rest on a surface; may include one or more camera holders configured to fix and support an optical camera and a thermal camera; a mobile device holder configured to support a mobile device; and may include a body part placement location configured to place an inspected body part and a reference or contralateral body part in such a location in which the optical camera and the thermal camera can capture image data and a thermogram, respectively, of the inspected body part and the reference body part.

Any of the foregoing embodiments may further include a processing unit configured to receive the image data and the thermogram and to determine that a functional disorder or inflammation of the inspected body part has occurred by comparing the thermogram corresponding to the inspected body part to the thermogram corresponding to the reference or contralateral body part.

In any of the foregoing embodiments, the processing unit includes: a processing unit control system configured to communicate with the mobile device; a database configured to store optical and thermal images and user account information; and a processor coupled to the processing unit and the database and to perform computing, analysis, and comparison of the optical image and the thermogram.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views, wherein:

DETAILED DESCRIPTION

Figure 1:
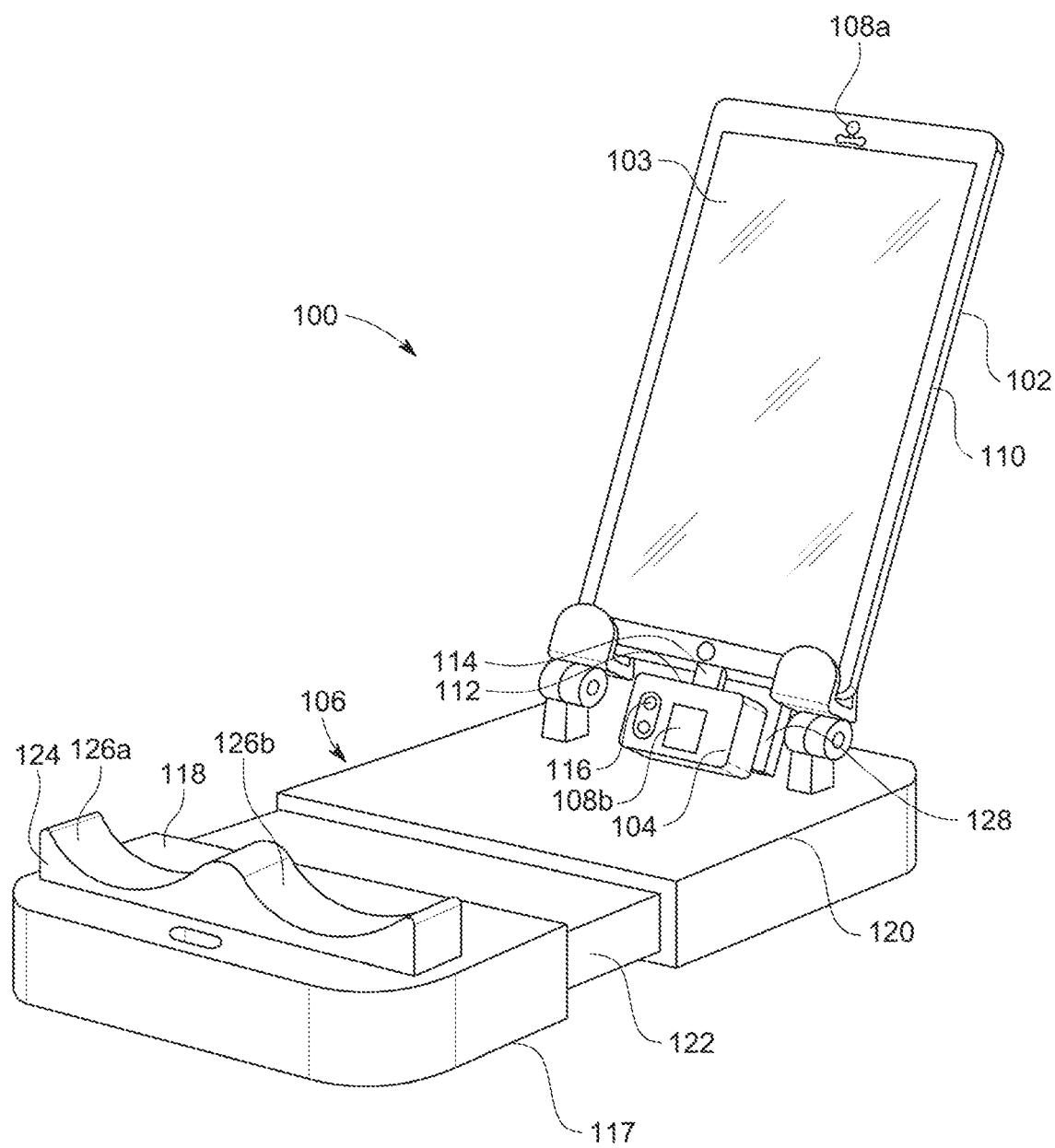
FIG. 1 illustrates a perspective view of a system for identifying a health disorder based on a temperature asymmetry estimation according to various embodiments of the present disclosure.

The systems, methods, and apparatus described herein may be used to identify a health disorder based on a temperature asymmetry estimation. The identified health disorder may be a functional disorder or an inflammation. Particularly, the identified health disorder may be arthritis (e.g., Rheumatoid Arthritis (RA), Osteoarthritis, or Psoriatic Arthritis). The systems may capture thermal images of an inspected body part and a reference body part of a person via a thermal camera. The capturing of the thermal images may be simultaneous. The systems may further capture optical images of the inspected body part and the reference body via an optical camera. The optical image capturing and the thermal image capturing may be simultaneous. The inspected body part may include, for example, a joint, a knee, an ankle, or the like. The reference body part may include a contralateral joint(e.g., a contralateral knee or ankle). The outlines of the inspected body part and the reference body part may be detected automatically. An exact comparison between slightly different, or asymmetric, body part outlines may be performed.

The thermal and optical cameras may be controlled by a mobile device. The thermal and optical images may be transmitted to a remote processor, which may be a processor of a remote server. The processor may analyze the thermal and optical images and advantageously determine that the inspected body is experiencing a functional disorder or an inflammation. The systems may detect small changes in the body part temperature. More specifically, the processor may estimate a recorded image displacement of the inspected body part and a recorded image displacement of the reference body part and compare the two estimates to make the determination that the body part is experiencing a health disorder. The estimation of the recorded image displacement of the inspected body part may be based on the optical image and thermal image of the inspected body part. The estimation of the recorded image displacement of the reference body part may be based on the optical image and thermal image of the reference body part. The exact area of inflammation or functional disorder may be mapped.

The systems may have an output device in communication with the processor to advantageously output data indicating that the body part is experiencing a health disorder. The systems may make recommendations as to next steps to follow based on the presence of an inflammation or functional disorder. The systems may have a database of stored thermograms, which may be viewed by the patient or a distant healthcare professional or administrator. Tests conducted using the systems may be self-administered. The systems may be advantageously used without requiring the help of another person or a healthcare professional. Alternately, the systems are advantageously suitable for use with the assistance of another person or a healthcare professional if needed. As such, the term "user" may refer to a patient, a healthcare professional, a guardian, a helper, a caregiver, or the like.

FIG. 1 illustrates a perspective view of a system 100 for identifying a health disorder based on a temperature asymmetry estimation according to various embodiments of the present disclosure. The system 100 may include a mobile device 102, an imaging device 104, and a base unit 106.

The mobile device 102 may be a cellular phone, a tablet, a laptop, or another portable computing device. The mobile device 102 may have a display 103. The display 103 may be a liquid crystal display (LCD), a light-emitting diode display (LED), an organic light emitting diode (OLED), a plasma display, a cathode-ray tube (CRT) display, a digital light processing display (DLPT), a microdisplay, a projection display, or any other display appreciated by one of ordinary skill in the art. The display 103 may display user interfaces, text, images, and/or the like. The interface may allow a user to control the mobile device 102 and one or more components of the system 100. The interface may further allow the user to view information outputted by the system 100. The display 103 may be touchscreen and used to input user commands. The mobile device 102 may have an optical camera 108a. The optical camera 108a may be located on a front side 110 of the mobile device 102 as shown in FIG. 1. In some embodiments, the optical camera 108a may be located on a rear side (not shown) of the mobile device 102, or may include a first optical camera on the front side 110 and a second optical camera on the rear side. The optical camera 108a may have an optical instrument to record or detect static or dynamic images. The optical camera 108a may have a lens that focuses reflected light from a body part of a person along with an image recording mechanism. The optical camera 108a may be integrated into the mobile device 102 as shown in FIG. 1. In some embodiments, the optical camera 108a may include separate hardware having a remote body attachable to the mobile device 102 or the system 100 in general. The attachment may utilize any one or more type of universal serial bus (USB) (e.g., micro USB, USB-C), lighting, or any other connection means. The connection may also or instead include a wireless connection utilizing Bluetooth, Infrared (IR), WiFi, or the like.

The mobile device 102 may be attached to the imaging device 104. The attachment may be an electronic attachment. An output device 112 of the imaging device 104 (e.g., a data or other port) may be coupled to an input device 114 of the mobile device 102 (e.g., another data or other port). The attachment between the imaging device 104 and the mobile device 102 may utilize one or more type of USB, lighting, or any other conventional connection means. The connection may also be a wireless connection utilizing Bluetooth, IR, WiFi, and the like. The imaging device 104 may have an optical camera 108b. The optical camera 108b may be used in lieu of, or in addition to, the optical camera 108a. The optical camera 108b may have the same or similar components to those of the optical camera 108a. In some embodiments, the system 100 may include at least one of the optical camera 108a or the optical camera 108b. The imaging device 104 may further have a thermal camera 116. The thermal camera 116 may have an optical instrument to record static or dynamic images using infrared radiation in the LWIR. The thermal camera 116 may have a thermal image sensor and an image recording mechanism. The thermal camera 116 may be integrated into the imaging device 104 as shown in FIG. 1, or may be provided separately. In some embodiments, the thermal camera 116 and the optical camera 108b may be stacked on top of each other.

The thermal camera 116 and the optical camera 108b may have the same appearance and exterior features. The thermal camera 116 and the optical camera 108b may be oriented vertically relative to each other as shown in FIG. 1. In some embodiments, the thermal camera 116 and the optical camera 108b may be oriented horizontally or diagonally relative to each other. In some embodiments, the thermal camera 116 may be or include separate hardware having a remote body attachable to the imaging device 104 or to another portion of the system 100. The attachment may utilize any one or more connection type such as USB, lighting, or any other conventional connection means. The connection may also be a wireless connection utilizing Bluetooth, IR, WiFi, or the like. In some embodiments, the thermal camera 116 may be integrated into the mobile device 102.

The mobile device 102 and the imaging device 104 may be mechanically attached (at least one of permanently or removably coupled) to the base unit 106. The base unit 106 may include metal, plastic, wood, and/or the like. The base unit 106 may be a unitary construction (i.e., formed monolithic) or composed of several parts coupled together using any known fastening technique (e.g., press-fit, screws, adhesives). The base unit 106 may be shaped and sized to be portable. The base unit 106 may be configured to have a substantially flat bottom surface 117. The substantially flat bottom surface 117 may allow the base unit 106 to rest on a surface. Preferably, the surface may be flat and smooth. The base unit 106 may have filleted edges. The filleted edges may be user friendly and allow the base unit 106 to be held with ease.

The base unit 106 may have a body portion 118 and a device portion 120. The body portion 118 and the device portion 120 may be connected to an extendable portion 122 situated in between the body portion 118 and the device portion 120. The extendable portion 122 may be attached to the body portion 118 and the device portion 120 via a sliding rail mechanism. The body portion 118 and the device portion 120 may be moved away from each other about the extendable portion 122 to extend the base unit 106. In some embodiments, the extendable portion 122 may include one or more separate attachments each having different lengths. The user may select an attachment based on a desired extension length. The desired extension length may depend on the user's size (e.g., height, length of limbs, joint size). The extension may allow the user to adhere to an image capture perimeter of the imaging device 104. For example, the imaging device 104 may require the images of the body parts to be inspected to fit within a virtual template having predetermined dimensions.

The body portion 118 may have a placement location 124 extending therefrom. The placement location 124 may be configured to receive and ensure proper placement of the user's arms, elbows, wrists, legs, knees, ankles, feet, or any other body part or pair of body parts. The placement location 124 may elevate the placed body parts from the body portion 118. In some embodiments, the elevation of the placement location 124 from the body portion 118 may be adjustable. The placement location 124 may have two resting surfaces 126a,b. The placed body parts may directly contact the resting surfaces 126a,b. The resting surfaces 126a,b may each have a curvature shaped and sized to accommodate the placed body parts while complementing the natural shape of the placed body parts.

The device portion 120 may have an imaging connector 128. The imaging connector 128 may be configured to be attached to the imaging device 104. The imaging connector 128 may hold the imaging device 104 in place relative to the placement location 124. This may allow the imaging device 104 to detect images of the body parts that have greater quality than can be detected without the imaging connector 128 due to being still during image capture. The imaging device 104 may be removably attached to the imaging connector 128. Any known non-permanent fastening techniques may be utilized to attach the imaging device 104 to the imaging connector 128 (e.g., insert, mounting clips, hooks, screws). The imaging connector 128 may be further configured to be attached to the mobile device 102. The mobile device 102 may be removably attached to the imaging connector 128. Any known non-permanent fastening techniques may be utilized to attach the mobile device 102 to the imaging connector 128 (e.g., insert, mounting clips, hooks, screws). The imaging connector 128 may be pivotally attached to the device portion 120 or have a pivoting body relative to the device portion 120. The pivotability of the imaging connector 128 may allow the mobile device 102 and the imaging device 104 to be angled as desired. The imaging connector 128 may elevate the mobile device 102 and/or the imaging device 104 from the device portion 120. The elevation of the mobile device 102 and the imaging device 104 from the device portion 120 may each be adjusted, either simultaneously or independently.

Figure 2:
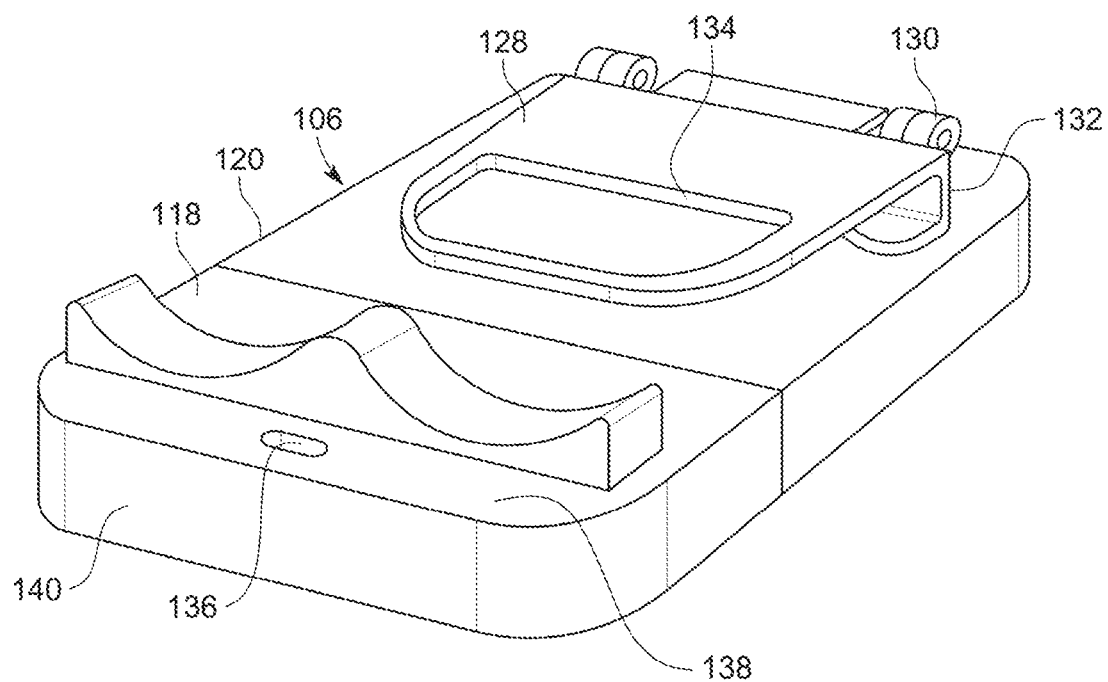
FIG. 2 illustrates a perspective view of a base unit of the system of FIG. 1 in a non-extended position and an imaging connector of the base unit in a closed position according to various embodiments of the present disclosure.

FIG. 2 illustrates a perspective view of the base unit 106 in a non-extended position and the imaging connector 128 in a closed position according to an aspect of the present disclosure. The imaging connector 128 may fold into the closed position when the system 100 is not being used but rather being stored or transported. The mobile device 102 and the imaging device 104 may have to be removed from the imaging connector 128 prior to bringing the imaging connector 128 to the closed position. The imaging connector 128 may be pivoted from a pivot joint 130 attaching the imaging connector 128 to an imaging connector base 132. In some embodiments, the pivot joint 130 may attach the imaging connector 128 directly to the base unit 106. In the closed position, the imaging connector 128 may be substantially parallel to the base unit 106. The imaging connector 128 may have an opening 134. The opening 134 may be shaped and sized to allow a user to grip the imaging connector 128 with one or more fingers to traverse the imaging connector 128 between the open position and the closed position. In some embodiments, the opening 134 may be replaced with a protrusion such as a handle or a ring attachment.

The body portion 118 and the device portion 120 may be flush in the non-extended position. The body portion 118 may have a cavity 136. The cavity 136 may be located on a top surface 138 of the body portion 118. The cavity 136 may be near a proximal end 140 of the body portion 118, the proximal end 140 being away from the device portion 120. The cavity 136 may allow the user to grip the body portion with one or more fingers to traverse the base unit 106 between the extended position and the non-extended position. The device portion 120 may also have a cavity (not shown) mirroring the cavity 136. The user may traverse the base unit 106 between the extended position and the non-extended position from the body portion 118, the device portion 120, or both. In some embodiments, the cavity 136 may be replaced with a protrusion.

Although various details have been provided regarding the base unit 106, this information is exemplary only. One skilled in the art will realize that any additional or alternative base unit may be used in order to capture images corresponding to various body parts. For example, a different base unit may be used to capture images corresponding to elbows.

Figure 3:
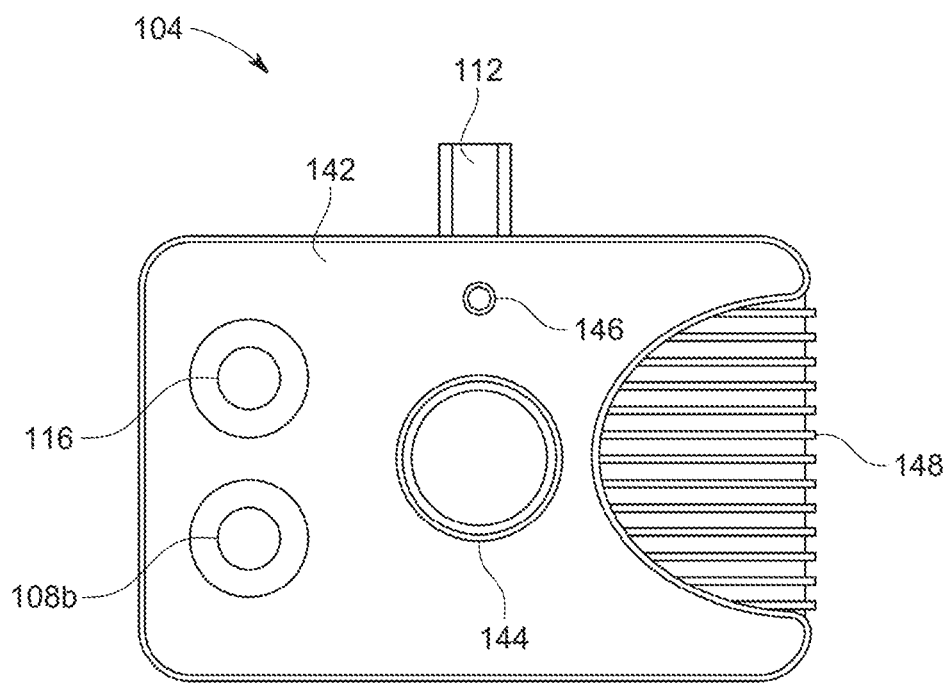
FIG. 3 illustrates a front isolated view of an imaging device of the system of FIG. 1 according to various embodiments of the present disclosure.

FIG. 3 illustrates a front isolated view of the imaging device 104 of the system 100 according to an aspect of the present disclosure. The imaging device 104 may have components attached together by, or enclosed within, a casing 142. The components may include the optical camera 108*b*, the thermal camera 116, the output device 112, an on/off switch 144, a power indicator light 146, a grip 148, and a charging port (not shown). The imaging device 104 may have a battery housed within the casing 142. The battery may be charged via the charging port, may be replaceable, or both. The charging port may receive all types of USB, lighting, and any other conventional power cords. In some embodiments, the imaging device 104 may use disposable batteries (e.g., AA, AAA). The power indicator light 146 may indicate whether the imaging device 104 is on, charged, charging, and/or needs charging. The power indicator light 146 may blink and/or emit a specific colored light associated with a power state. The power indicator light 146 may be a light emitting diode (LED). The on/off switch 144 may be used to power on and off the imaging device 104. In some embodiments, the on/off switch 144 may also be used to capture images via the optical camera 108*b* and/or the thermal camera 116. The on/off switch 144 may receive a plurality of inputs by a variety of ways of activating the on/off switch 144 (e.g., pressing a certain number of times, pressing and holding, pressing all the way in, sliding). The grip 148 may be a rough surface on the casing 142. The grip 148 may extend to a plurality of sides of the casing 142. The grip 148 may allow the user to comfortably hold the imaging device 104 without covering the optical camera 108*b* or the thermal camera 116, thereby mitigating drops and reducing the likelihood of unwanted fingerprint marks on the optical camera 108*b* and the thermal camera 116.

Figure 4:
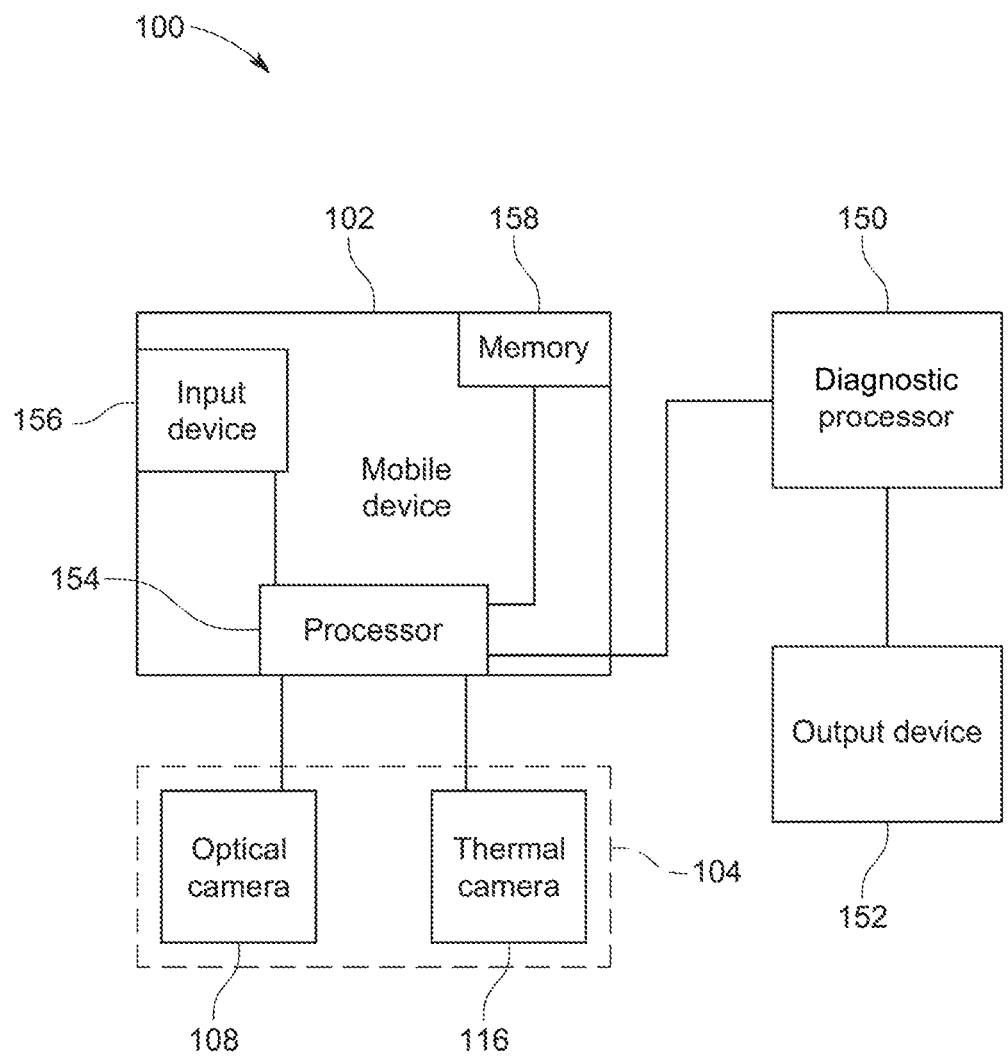
FIG. 4 is a block diagram illustrating various components of the system of FIG. 1 according to various embodiments of the present disclosure.

FIG. 4 is a block diagram illustrating various components of the system 100 according to an aspect of the present disclosure. The system 100 may include the mobile device 102, the imaging device 104, a diagnostic processor 150, and an output device 152. The mobile device 102 may have a processor 154. The processor 154 may be configured to execute machine-readable instructions. In some embodiments, there may be a plurality of processors 154. The processor 154 may be a microprocessor or a microcontroller by example. The processor 154 may be programmed to control the thermal camera and/or the optical camera to detect the thermal images and/or the optical images based on the user's input.

The user input may be received via an input device 156. The input device 156 may be integrated to the mobile device 102. The input device 156 may receive visual, auditory, and/or touch input. For example, the input device 156 may be a camera, a microphone, a touchscreen, a button, or a remote. The input device 156 may be integrated with the display 103 of the mobile device 102. The input device 156 may receive biometric information, the user's voice, and/or the user's touch input with one or more fingers. The input may be a request to begin image capture.

In some embodiments, the mobile device 102 may be controlled automatically using an algorithm stored in a memory 158. The memory 158 may be non-transitory and may include one or more of a random-access memory (RAM), a disk, a flash memory, optical disk drives, hybrid memory, or any other storage medium that can store data. The memory 158 may store program code that are executable by the processor 154. The memory 158 may store data in an encrypted or any other suitable secure form. The mobile device 102 may be controlled to begin detecting images as soon as a known or recognized image is in the field of view of the optical camera 108 and/or the thermal camera 116. After images are detected, the mobile processor 154 may transmit the images to the diagnostic processor 150.

The diagnostic processor 150 may have diagnostic, monitoring, and prognostic capabilities. The diagnostic processor 150 may be part of a remote computer or part of a remote server. The diagnostic processor 150 may communicate with the mobile device 102 wirelessly or by a wired connection. The wireless communication may be through internet, WiFi, Bluetooth, IR, or the like. In some embodiments, some or all of the aforementioned communication methods may be available for selection of the user based on preference or suitability (e.g., signal travel distance, signal availability, signal interference, signal travel speed). The wired communication may use all types of USB, lighting, and the like. In some embodiments, the diagnostic processor 150 may be integrated to the mobile device 102. The diagnostic processor 150 may be implemented on a plurality of computers connected in a network or a plurality of virtual machines in a could infrastructure. The remote computer or the remote server may store, analyze, and compare the transmitted images. The remote computer or the remote server may store data including optical and thermal images, files, and user account information. The diagnostic processor 150 may identify an outline of the inspected body part and the reference body part, evaluate temperature differences, and determine that a functional disorder or inflammation of the inspected body part has occurred among other things. The diagnostic processor 150 may use filtering technologies and advanced statistical models to perform some or all of its functions. In some embodiments, machine learning and artificial intelligence may be utilized to perform some or all of its functions. The diagnostic processor 150 may send feedback to the mobile device 102 and/or the output device 152. In some embodiments, the diagnostic processor 150 may not be present such that all actions described herein regarding the diagnostic processor 150 are instead performed by the processor 154.

The output device 152 may be configured to output status data corresponding to the imaging device 104. The status data may include optical and thermal images detected by the imaging device 104 and/or data outputted by the diagnostic processor 150 upon conducting an analysis of the optical and thermal images. The status data may further include optical images of the patient's positioning, or joint placement relative to the imaging device 104, to ensure the imaging device 104 and the base unit 106 are being used correctly. The output device 152 may present the status data visually or auditorily. The status data may also include instructions to the user to reposition themselves to optimize detection of optical and thermal images. The output device 152 may be a display (e.g., touchscreen), a speaker, or the like. The display may be a liquid crystal display (LCD), a light-emitting diode display (LED), an organic light emitting diode (OLED), a plasma display, a cathode-ray tube (CRT) display, a digital light processing display (DLPT), a micro-display, a projection display, or any other display appreciated by one of ordinary skill in the art. The display may display user interfaces, text, images, and/or the like. In some embodiments, the output device 152 may be integrated with the mobile device 102 or the imaging device 104. The output device 152 may communicate with the diagnostic processor 150 wirelessly or by a wired connection. The wireless communication may be through internet, WiFi, Bluetooth, IR, or the like. In some embodiments, some or all of the aforementioned communication methods may be available for selection of the user based on preference or suitability (e.g., signal travel distance, signal availability, signal interference, signal travel speed). The wired communication may use all types of USB, lighting, and the like.

The status data may also or instead be directly transmitted to a healthcare professional who is assigned to monitor the joints or overall health of the user. The transmission may be conducted via email, phone, text message, software notification, or another means of data transfer. In some embodiments, the status data may be encrypted during transmission and decrypted once received. When the user and/or his/her assigned healthcare professional receives the feedback about the health state of the joints and whether the user captured the optical and thermal images properly, they can make a diagnosis and determine an appropriate course of treatment or action.

Figure 5A:
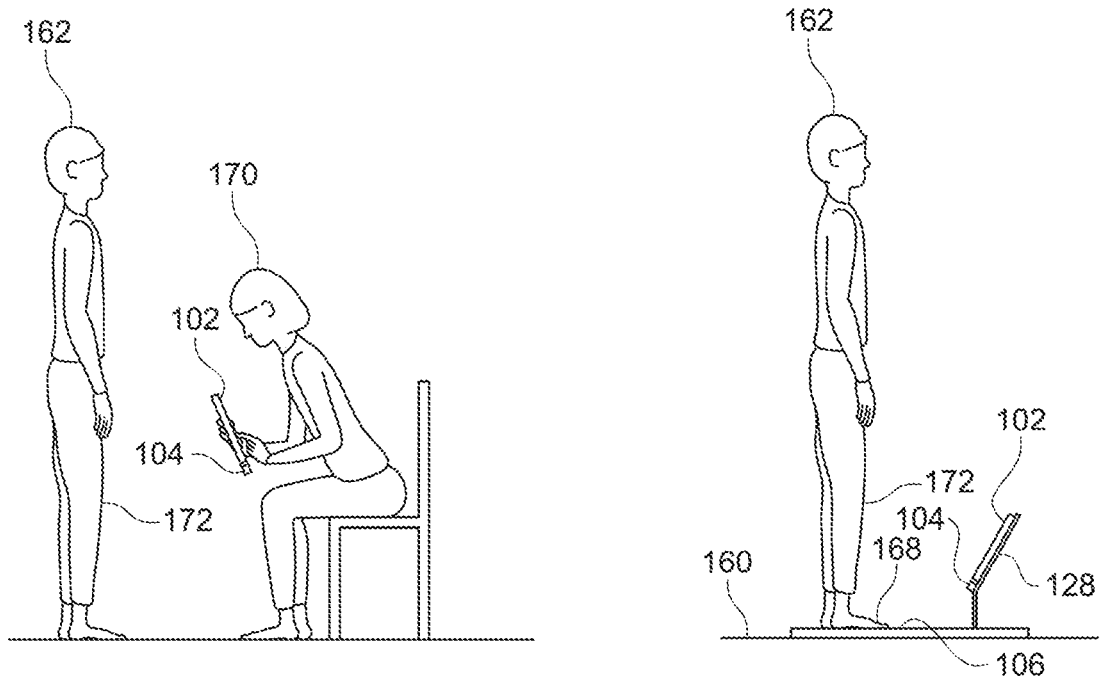
FIG. 5A illustrates methods of using the system of FIG. 1 according to various embodiments of the present disclosure.

FIG. 5A illustrates methods of using the system 100 according to an aspect of the present disclosure. On a left side of FIG. 5A, a patient 162 and an aide 170 are shown. The patient 162 may be in a standing position. The aide 170 may hold the imaging device 104 and, in some embodiments, the mobile device 102 coupled to the imaging device 104 to capture optical and thermal images of the knees 172 of the patient 162. The aide 170 may be in a seated position to hold the imaging device 104 at a close proximity to the knees 172. In some embodiments, the aide 170 may crouch or lower the imaging device 104 to or near the level of the knees 172 with an extension attachment from a standing position. The aide 170 may use the output device 152, which may be the mobile device 102 or the imaging device 104, to receive feedback of the analysis (see FIG. 4).

On a right side of FIG. 5A, only the patient 162 is shown. The patient 162 may self-inspect his/her knees 172. The patient 162 may be in a standing position. The patient 162 may stand on the base unit 106. The base unit 106 may be placed on a flat surface 160 such as the ground. In some embodiments, the base unit 106 may have designated locations (e.g., cavities, platforms, markings, protrusions, etc.) to place the feet 168 of the patient 162. The designated locations may provide consistency and accuracy in image capturing by ensuring the patient 162 positions himself/herself in a desired manner relative to the imaging device 104 and ensuring that the positioning remains consistent. The imaging connector 128 may be elevated from the base unit 106 such that the imaging device 104 is at a close proximity to the knees 172. The imaging connector 128 may be tilted towards the patient 162 such that the imaging device 104 and, in some embodiments, the mobile device 102 are facing the knees 172. The patient 162 may autonomously initiate the capturing of the optical and thermal images in various ways. For example, the patient 162 may set a timer for the imaging device 104 to capture images after a certain time period has lapsed, which gives the patient 162 enough time to position himself/herself. In another example, the patient 162 may perform a motion in front of the imaging device 104 (e.g., a wave, making a fist, etc.) once in position to initiate the capturing of the images. In yet another example, the patient 162 may have a remote device in communication with the imaging device 104 that the patient 162 can input an image capture signal. The remote device may be the input device 156 (see FIG. 4).

Figure 5B:
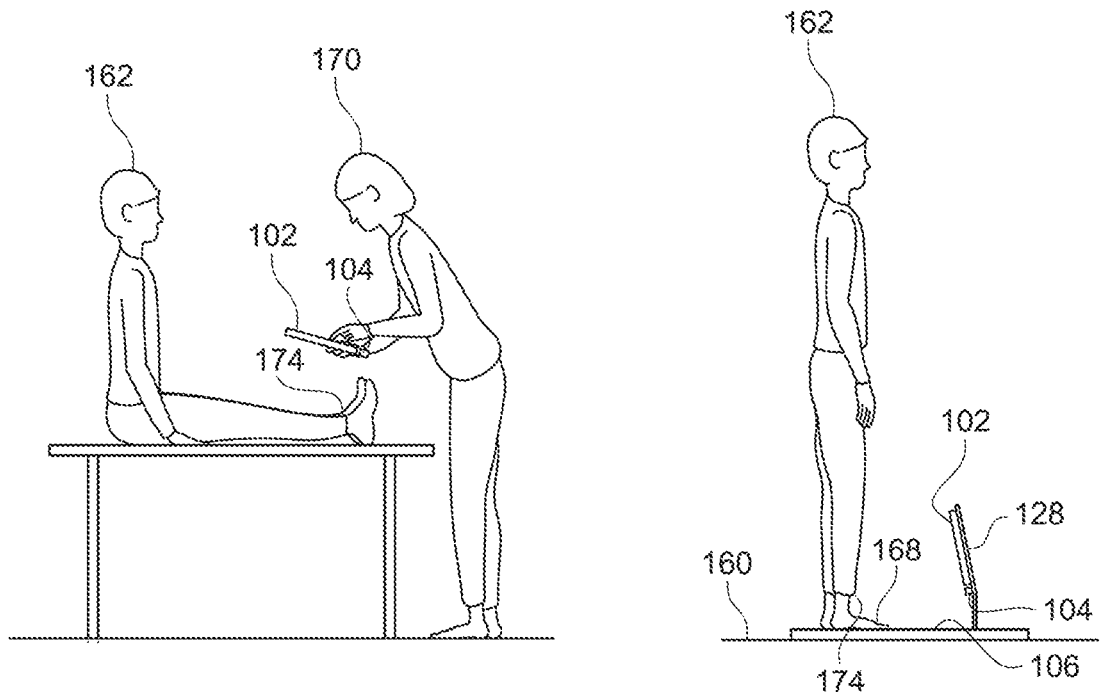
FIG. 5B illustrates methods of using the system of FIG. 1 according to various embodiments of the present disclosure.

FIG. 5B illustrates methods of using the system of FIG. 1 according to an aspect of the present disclosure. On a left side of FIG. 5B, a patient 162 and an aide 170 are shown. The patient 162 may lie down if desired or necessary. The aide 170 may hold the imaging device 104 and, in some embodiments, the mobile device 102 coupled to the imaging device 104 to capture optical and thermal images of the ankles 174 of the patient 162. The aide 170 may be in a standing position to hold the imaging device 104 at a close proximity to the ankles 174. In some embodiments, the aide 170 may bend or lower the imaging device 104 above the ankles 174 with an extension attachment from a standing position. The aide 170 may use the output device 152, which may be the mobile device 102 or the imaging device 104, to receive feedback of the analysis (see FIG. 4).

On a right side of FIG. 5B, only the patient 162 is shown. The patient 162 may self-inspect his/her ankles 174. The patient 162 may be in a standing position. The patient 162 may stand on the base unit 106. The base unit 106 may be placed on a flat surface 160 such as the ground. In some embodiments, the base unit 106 may have designated locations (e.g., cavities, platforms, markings, protrusions, etc.) to place the feet 168 of the patient 162. The designated locations may provide consistency and accuracy in image capturing by ensuring the patient 162 positions himself/herself in a desired manner relative to the imaging device 104. The imaging connector 128 may be elevated from the base unit 106 such that the imaging device 104 is at a close proximity to the ankles 174. The imaging connector 128 may be tilted towards the patient 162 such that the imaging device 104 and, in some embodiments, the mobile device 102 are facing the ankles 174. The patient 162 may autonomously initiate the capturing of the optical and thermal images in various ways. For example, the patient 162 may set a timer for the imaging device 104 to capture images after a certain time period has lapsed, which gives the patient 162 enough time to position himself/herself. In another example, the patient 162 may perform a motion in front of the imaging device 104 (e.g., a wave, making a fist, etc.) once in position to initiate the capturing of the images. In yet another example, the patient 162 may have a remote device in communication with the imaging device 104 that the patient 162 can input an image capture signal. The remote device may be the input device 156 (see FIG. 4).

Figure 6A:
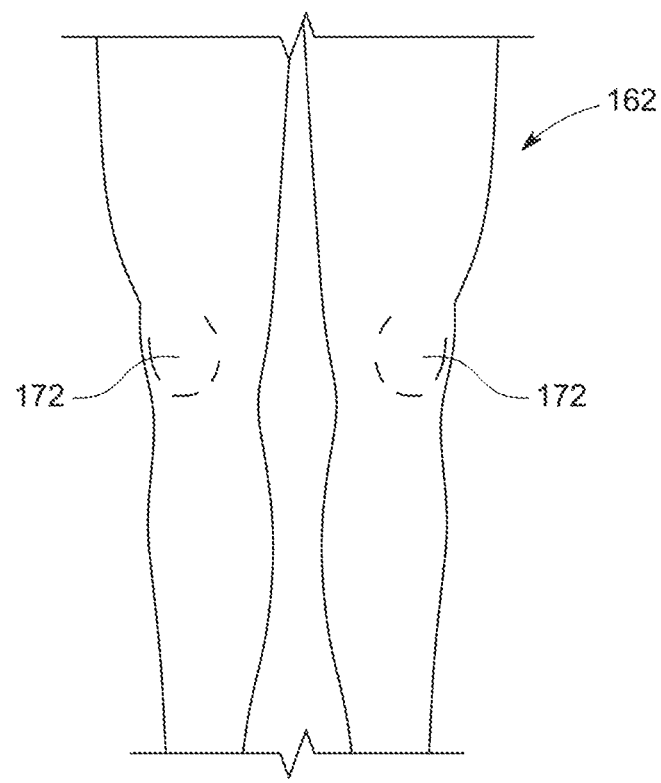
FIG. 6A illustrates an optical image of knees of a patient according to various embodiments of the present disclosure.
Figure 6B:
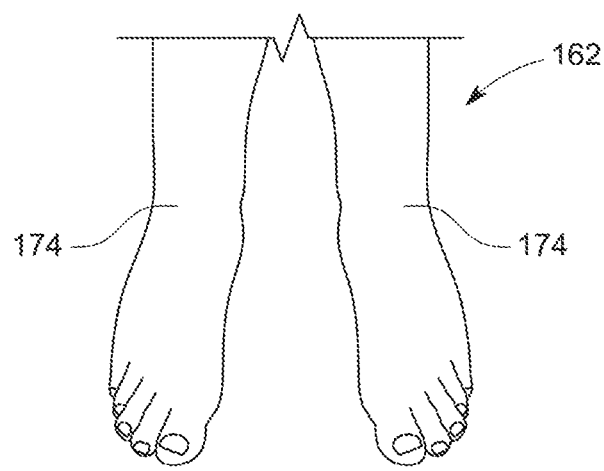
FIG. 6B illustrates an optical image of ankles of the patient according to various embodiments of the present disclosure.

FIG. 6A illustrates an optical image of the knees 172 of the patient 162 according to an aspect of the present disclosure. FIG. 6B illustrates an optical image of the ankles 174 of the patient 162 according to an aspect of the present disclosure. During the measurement, the knees 172 and the ankles 174, or the joints, may be photographed in such a way that they have a length of about 480 pixels and a width of about 260 pixels considering the thermogram resolution 640×480 pixels, so the joints' outline may have 480*260*0.9=112320 pixels. Here, 0.9 is a ratio that takes into account the influence of the roundness of the joints on the joints area. Grid of points of interest may be distributed in regular way taking in to account cells size as a division of the length of the identified joint by 100, i.e. the joint grid height is said to be 100 cells. Then the width of the joint would be about 55 cells. Therefore, the joint area will be equal to 100*55*0.95=5225 cells. If the above mentioned joints' outline length is 480 pixels, the cell size value will be equal (480/260)^2=16 pixels of the thermal imager (approximately one unit of temperature per square millimeter (mm$^2$)). This means that 5225*16=83600 points of the thermal imager are involved in the evaluation of the joint. However, lower resolution (generalized data) with 16 values per square centimeter (cm$^2$) may be used for evaluation, so that the cell size is about $2.5^{-3} \times 2.5^{-3}$ mm$^2$. In principle, cell size can be reduced even more times while increasing the measurement resolution, but this may increase the probability of false-positive inflammation detection cases, when a change of a temperature of a small area would be treated as a pathology. Selected cell size is relative and may be selected based on real data for optimal performance.

Figure 7:
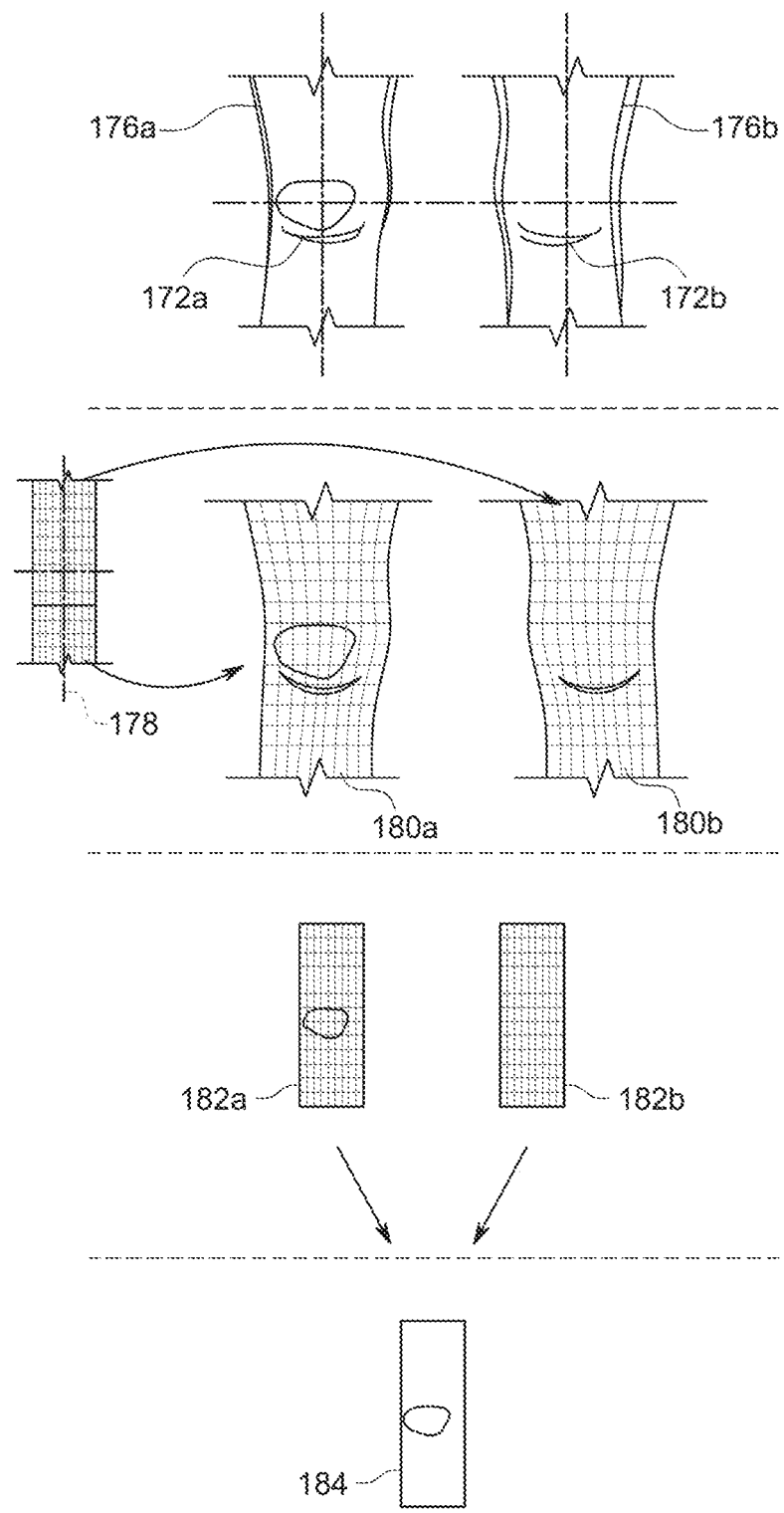
FIG. 7 illustrates a method of obtaining a temperature difference map of the knees of the patient according to various embodiments of the present disclosure.

FIG. 7 illustrates a method of obtaining a temperature difference map of the knees 172 of the patient 162 according to an aspect of the present disclosure. A similar method for other joints such as ankles, wrists, elbows, etc. are also contemplated. The inspected knee 172a and the contralateral knee 172b are shown in FIG. 7. After fine tuning, a fitted template 176a for the inspected knee 172a may be obtained. Similarly, after fine tuning, a fitted template 176b for the contralateral knee 172b may be obtained. An initial grid template 178 is also shown in FIG. 7. The initial grid template 178 may be applied for both the inspected knee 172a and the reference knee 172b. As a result, an inspected knee grid template 180a and a contralateral knee grid template 180b may be obtained. Then, temperature maps 182a,b for both the inspected knee 172a and the contralateral knee 172b may be estimated according to the appropriate set of points of interest. Estimation of a temperature disparity map may be performed by subtracting the temperature values in the contralateral knee temperature map 182b from the appropriate temperature values in the inspected knee temperature map 182a, and the temperature difference map (i.e., temperature disparity map) 184 may be obtained. The temperature difference map 184 may show the temperature differences between the inspected knee 172a and the contralateral knee 172b, and these temperature differences may be set for different values. If the temperature differences surpass a medically based threshold value, the temperature asymmetry may indicate an inflammation or a functional disorder, such as arthritis.

Figure 8:
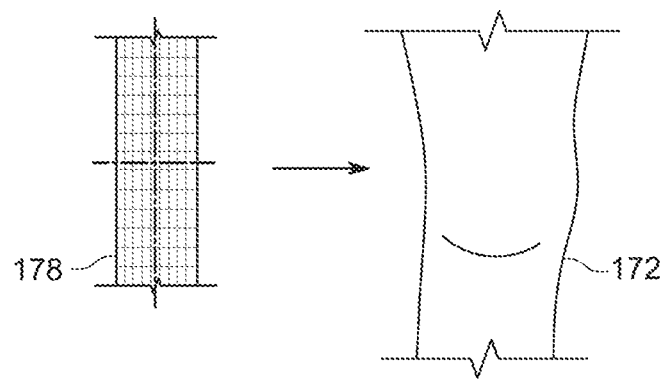
FIG. 8 illustrates a method of fine tuning a knee template according to various embodiments of the present disclosure.
Figure 8:
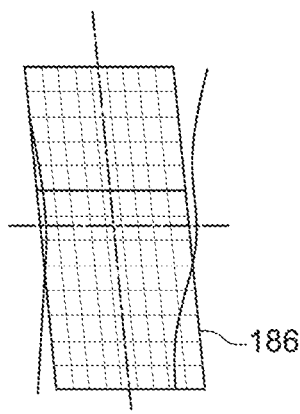
Figure 8:
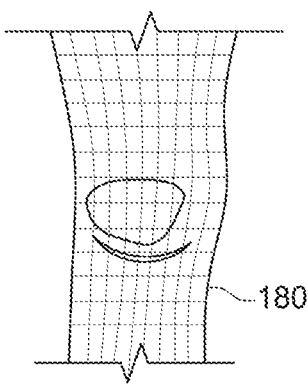

FIG. 8 illustrates a method of fine tuning a knee template according to an aspect of the present disclosure. An initial grid template 178 and a knee 172 are shown in FIG. 8. First, a rigid transformation may be performed to obtain a rigid transformation knee template 186. Rigid transformation parameters, scale, rotation, translation, and mirror, may be estimated by solving the optimization problem descent gradient method. Rigid transformation obtained may be defined as a 4×4 transformation matrix. Since the rigid transformation knee template 186 is inaccurate due to its inability to fit the knee template to a specific knee outline, a non-rigid transformation may be performed. Two coefficients vectors may be used to represent the non-rigid transformation. Following the non rigid-transformation, an accurate knee grid template 180 may be obtained.

Figure 9:
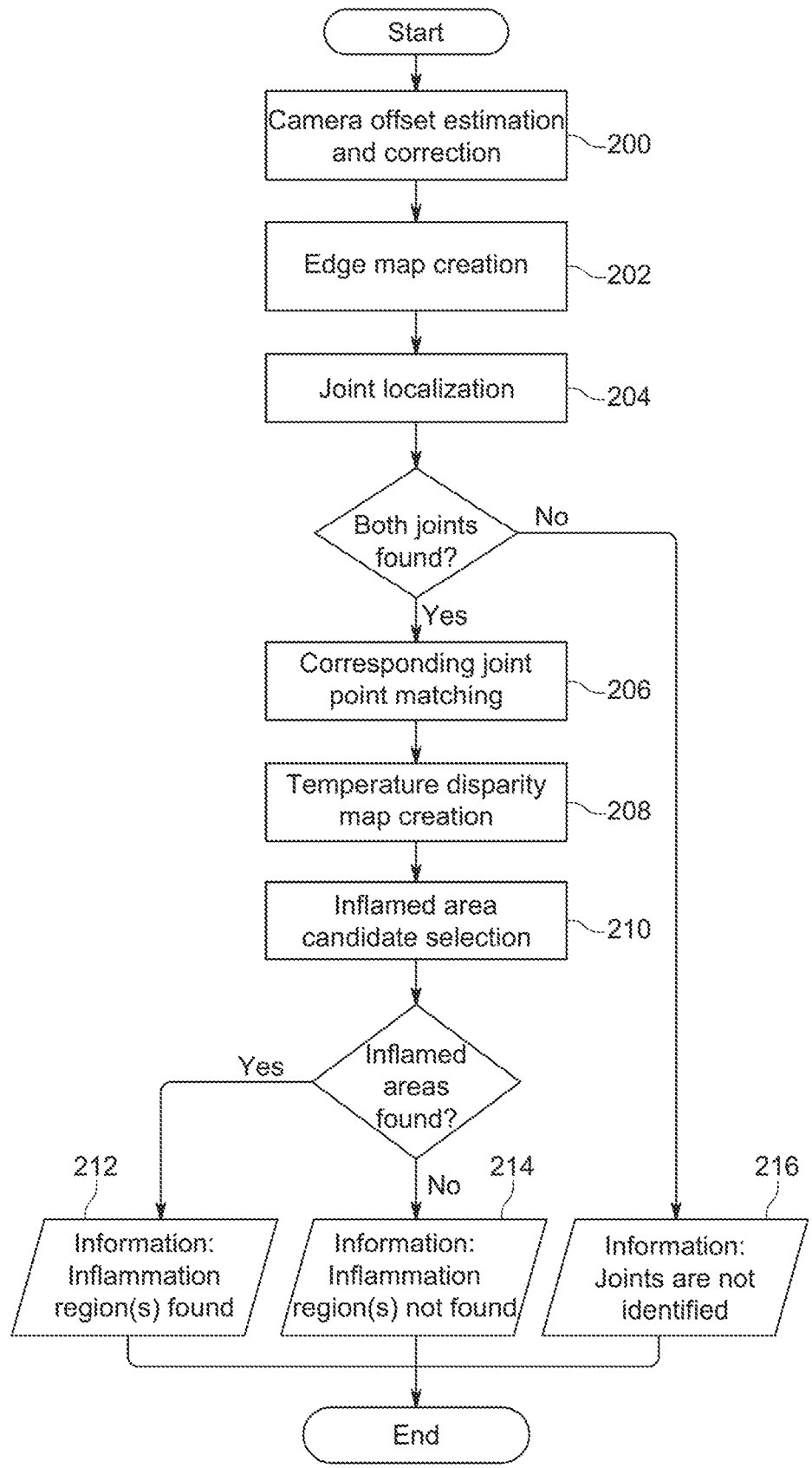
FIG. 9 illustrates an algorithm to detect arthritis based on temperature asymmetry estimation in joints according to various embodiments of the present disclosure.

FIG. 9 illustrates an algorithm to detect arthritis based on temperature asymmetry estimation in joints according to an aspect of the present disclosure. The process may be performed by the processor 154 (see FIG. 4). The process may begin with a camera offset estimation and correction in block 200. In block 200, first, a thermal image, or a thermogram, and an optical image of the inspected joint and the contralateral joint may be captured simultaneously. Then, the thermal and optical images may be temporally aligned. Then, a displacement between the thermal and optical images may be estimated, and the optical image may be aligned to the thermal image. Keypoints may be located in both the thermogram and the optical image. It is desirable for the keypoints to be clearly visible both in the thermogram and the optical image (e.g. sharp edges), and it is desirable for the keypoints to represent the same object or part thereof. By solving the optimization problem in any widely known way (e.g. Descent Gradient, Genetic Algorithm, etc.), the offset may be obtained by adjusting the thermogram and the optical image in such a way that the total nonconformity error between corresponding pairs of keypoints become minimal. The nonconformity error may be calculated as an error function representing the distance between corresponding pairs of keypoints in any known or other method (e.g., Root Mean Square Error). Then, the thermal and optical images may be both spatially and temporally aligned.

In block 202, an edge map may be created. First, an edge map may be computed for the optical and thermal images. Then, the two edge maps may be combined into one edge map. The resulting single edge map may contain information from both the thermal and optical images.

In block 204, joint localization may take place. First, a transformation best matching a base inspected joint template to an inspected joint outline and a base contralateral joint template to a contralateral joint outline in the combined edge map may be estimated. Then, the inspected joint and the contralateral joint may be localized. Transformation parameters (such as scale, rotation, translation, mirror, shear, etc.) may be estimated by solving the optimization problem in any known way (e.g. Descent Gradient, Genetic Algorithm, etc.). Body part templates compliancy may be estimated in any known way of vector line correspondence to line or edge represented in image (e.g. Edge detection etc.). Deformable Templates matching may be used to identify the outline of inspected and contralateral joint outlines in the thermogram and the optical image. Then, the localized inspected joint template to the inspected joint outline and the localized contralateral joint template to the contralateral joint outline in the combined edge map may be fine-tuned. During the fine-tuning process, the points of the inspected joint template transformed with localization transformation may be matched with the joint outline line or edge to achieve an optimal fit. However, the anatomical joint shape may be preserved by using accumulated reciprocal positions of corresponding points in a previously analyzed joint shape. Thus, the joint shape may be obtained by fitting the body part shape on the thermogram and the optical image.

If both the inspected joint and the contralateral joints are found, the process may continue with block 206. In block 206, corresponding joint point matching may take place. An inspected joint grid may be created by applying the transformation obtained from the fine tuned inspected joint template and the base inspected joint template to the base inspected joint grid. Similarly, a contralateral joint grid may be created by applying the transformation obtained from the fine-tuned contralateral joint template and the base contralateral joint template to the base contralateral joint grid. Then, a grid of key points of the inspected joint and a grid of key points of the contralateral joint are created.

In block 208, a temperature disparity map may be created. An inspected joint thermal map may be created by collecting thermal data from the thermal image according to the inspected joint grid. Similarly, a contralateral joint thermal map may be created by collecting thermal data from the thermal image according to the contralateral joint grid. Each value of the temperature maps is estimated by generalizing temperature values situated near the position of points of interest in the thermogram of the appropriate joint. Any known type of temperature values generalization may be used (e.g. mean, median, weighted mean, etc.). Then, an inspected joint thermal disparity map may be created by subtracting the contralateral joint thermal map from the inspected joint thermal map. Likewise, a contralateral joint thermal disparity map may be created by subtracting the inspected joint thermal map from the contralateral thermal map.

In block 210, an inflamed area candidate selection may be made. Candidate inflammation or functional disorder regions may be composed of the nearby points of the temperature disparity map exceeding a medically based threshold. The threshold may be found in medical literature, set by a researcher or doctor, or found via any other method. A descriptive feature vector may be created for each candidate inflammation or functional disorder region composed of estimations of generalized values of points, interposition, temperatures, or any combination thereof. A threshold inspected joint disparity map may be created according to medically significant thermal disparity value. Similarly, a threshold contralateral joint disparity map may be created according to the medically significant thermal disparity value. Then, an inspected joint approved inflammations list may be created by evaluating candidate inflammations in the inspected joint candidate inflammations lists. Likewise, a contralateral joint approved inflammations list may be created by evaluating candidate inflammations in the contralateral joint candidate inflammations lists. A final decision may be made by estimating approved inflammations amount in both lists.

If an inflamed area or inflamed areas are found, the process may continue with block 212. In block 212, the system 100 may notify the user that an inflammation region or inflammation regions were found. Analysis of inflammation or functional disorder regions may be performed by examining the feature vectors. During this process, non-confident inflammation or functional disorder regions may be rejected in order to clear the list against accidentally marked non-inflammable regions (e.g. the area deemed too small, or having a relatively small temperature excess, etc.). For better compliancy, any historically accumulated data may be used to perform this task. Any type of classificatory or machine learning functional step may be used to perform this task (e.g. support vector machine, artificial neural network etc.).

If an inflamed area is not found, the process may continue with block 214. In block 214, the system 100 may notify the user that an inflammation region was not found.

If both the inspected joint and the contralateral joints are not found, the process may continue with block 216. In block 216, the system 100 may notify the user that both joints were not found. In some embodiments, if both the inspected joint and the contralateral joints are not found, the system 100 may inform the user to wait and repeat the process. For example, the user may be informed to wait 15 minutes.

Where used throughout the specification and the claims, "at least one of A or B" includes "A" only, "B" only, or "A and B." Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for detection of arthritis based on temperature asymmetry estimation in joints, the method comprising:
    recording, using an optical camera and a thermal camera each coupled to a base unit via at least one connector, an optical image and a thermogram corresponding to a first joint of the joints and an optical image and a thermogram corresponding to a second joint of the joints, the second joint being contralateral to the first joint;

facilitating at least one of extension or contraction of an extendable portion of the base unit located between a body portion of the base unit and at least one connector to adjust a distance between the body portion and at least one of the first joint or the second joint;

receiving, by a processing unit, the optical image and the thermogram corresponding to the first joint and the optical image and the thermogram corresponding to the second joint;

estimating, by the processing unit, a recorded image displacement based on the thermogram and the optical image corresponding to the first joint to align the thermogram corresponding to the first joint and the optical image corresponding to the first joint, and estimating a recorded image displacement based on the thermogram and the optical image corresponding to the second joint to align the thermogram corresponding to the second joint and the optical image corresponding to the second joint; and determining, by the processing unit, that arthritis of the first joint has occurred by comparing the thermogram corresponding to the first joint to the thermogram corresponding to the second joint based on the recorded image displacement corresponding to the first joint and the recorded image displacement corresponding to the second joint.

2. The method of claim 1, wherein estimating the recorded image displacement corresponding to the first joint includes localizing a template of the first joint by locating corresponding pairs of keypoints in the optical image and in the thermogram, and calculating a nonconformity error between the corresponding pairs of keypoints in the optical image and in the thermogram.

3. The method of claim 2, wherein estimating the recorded image displacement further includes fine tuning by fitting a shape of the first joint on the thermogram and the optical image.

4. The method of claim 3, wherein estimating the recorded image displacement corresponding to the second joint includes localizing a reference template of the second joint by locating corresponding pairs of reference keypoints in the optical image and in the thermogram, and calculating a nonconformity error between the corresponding pairs of reference keypoints in the optical image and in the thermogram.

5. The method of claim 4, wherein estimating the recorded image displacement corresponding to the second joint further includes fine tuning by fitting a reference shape of the second joint on the thermogram and the optical image.

6. The method of claim 1, wherein the thermogram and the optical image are recorded simultaneously.

7. The method of claim 1, wherein determining that the arthritis of the first joint has occurred includes rejecting non-confident arthritis regions.

8. The method of claim 1, wherein determining that the arthritis of the first joint has occurred includes estimating temperature maps for the first joint and the second joint based on the thermogram of the first joint and based on the thermogram of the second joint.

9. The method of claim 8, wherein comparing the thermogram corresponding to the first joint to the thermogram corresponding to the second joint includes comparing the estimated temperature maps.

10. The method of claim 1, further comprising transmitting, by a network access device, a notification to a remote device associated with a healthcare worker indicating that occurrence of the arthritis of the first joint is determined.

11. The method of claim 1, further comprising recording, using the optical camera, an optical image of a patient to verify that a position of the patient conforms with a requisite position.

12. The method of claim 1, wherein the first joint and the second joint are supported by a body portion of the base unit.

13. The method of claim 1, further comprising facilitating angling of at least one of the optical camera or the thermal camera relative to at least one of the first joint or the second joint via a pivotable attachment between the at least one connector and a body portion of the base unit.

14. A method for detection of arthritis based on temperature asymmetry estimation in joints, the method comprising:

recording, using an optical camera and a thermal camera, an optical image and a thermogram corresponding to a first joint of the joints and an optical image and a thermogram corresponding to a second joint of the joints, the second joint being contralateral to the first joint;

receiving, by a processing unit, the optical image and the thermogram corresponding to the first joint and the optical image and the thermogram corresponding to the second joint;

estimating, by the processing unit, a recorded image displacement based on the thermogram and the optical image corresponding to the first joint, estimating the recorded image displacement corresponding to the first joint including localizing a template of the first joint by locating corresponding pairs of keypoints in the optical image and in the thermogram and calculating a nonconformity error between the corresponding pairs of keypoints in the optical image and in the thermogram, and estimating the recorded image displacement corresponding to the first joint further including fine tuning by fitting a shape of the first joint on the thermogram and the optical image;

estimating a recorded image displacement based on the thermogram and the optical image corresponding to the second joint, estimating the recorded image displacement corresponding to the second joint including localizing a reference template of the second joint by locating corresponding pairs of reference keypoints in the optical image and in the thermogram and calculating a nonconformity error between the corresponding pairs of reference keypoints in the optical image and in the thermogram, and estimating the recorded image displacement corresponding to the second joint further including fine tuning by fitting a reference shape of the second joint on the thermogram and the optical image; and determining, by the processing unit, that arthritis of the first joint has occurred by comparing the thermogram corresponding to the first joint to the thermogram corresponding to the second joint based on the recorded image displacement corresponding to the first joint and the recorded image displacement corresponding to the second joint.

15. The method of claim 14, wherein determining that the arthritis of the first joint has occurred includes rejecting non-confident arthritis regions.

16. The method of claim 14, wherein determining that the arthritis of the first joint has occurred includes estimating temperature maps for the first joint and the second joint based on the thermogram of the first joint and based on the thermogram of the second joint.

17. A method for detection of arthritis based on temperature asymmetry estimation in joints, the method comprising:

recording, using an optical camera and a thermal camera, an optical image and a thermogram corresponding to a first joint of the joints and an optical image and a thermogram corresponding to a second joint of the joints, the second joint being contralateral to the first joint, the optical camera and the thermal camera being coupled to a base unit via at least one connector while the optical image and the thermogram are recorded;

facilitating angling of at least one of the optical camera or the thermal camera relative to at least one of the first joint or the second joint via a pivotable attachment between the at least one connector and a body portion of the base unit;

receiving, by a processing unit, the optical image and the thermogram corresponding to the first joint and the optical image and the thermogram corresponding to the second joint;

estimating, by the processing unit, a recorded image displacement based on the thermogram and the optical image corresponding to the first joint and a recorded image displacement based on the thermogram and the optical image corresponding to the second joint; and determining, by the processing unit, that arthritis of the first joint has occurred by comparing the thermogram corresponding to the first joint to the thermogram corresponding to the second joint based on the recorded image displacement corresponding to the first joint and the recorded image displacement corresponding to the second joint.

18. The method of claim 17, further comprising facilitating at least one of extension or contraction of an extendable portion of the base unit located between a body portion of the base unit and the at least one connector to adjust a distance between the body portion and at least one of the first joint or the second joint.

* * * * *